(12) United States Patent
Rees et al.

(10) Patent No.: US 11,835,364 B2
(45) Date of Patent: Dec. 5, 2023

(54) SENSOR HOUSING WITH DEBRIS SLOUGHING STRUCTURE

(71) Applicant: Hadronex, Inc., Escondido, CA (US)

(72) Inventors: David B Rees, Encinitas, CA (US); Ronald Wayne Toten, Laguna Niguel, CA (US); Lawrence Brian Merchell, San Marcos, CA (US)

(73) Assignee: HADRONEX, INC., Escondido, CA (US)

( * ) Notice: Subject to any disclaimer, the term of this patent is extended or adjusted under 35 U.S.C. 154(b) by 319 days.

(21) Appl. No.: 17/163,252

(22) Filed: Jan. 29, 2021

(65) Prior Publication Data

US 2021/0231469 A1    Jul. 29, 2021

Related U.S. Application Data

(60) Provisional application No. 62/967,531, filed on Jan. 29, 2020.

(51) Int. Cl.
*G01D 11/24* (2006.01)
*G01N 33/00* (2006.01)
*G01S 7/02* (2006.01)

(52) U.S. Cl.
CPC ......... *G01D 11/245* (2013.01); *G01N 33/004* (2013.01); *G01N 33/0044* (2013.01); *G01N 33/0047* (2013.01); *G01S 7/02* (2013.01); *G01S 7/027* (2021.05)

(58) Field of Classification Search
CPC ...... G01D 11/24; G01D 11/245; G01D 11/30; G01N 33/004; G01N 33/0044; G01N 33/0047; G01S 7/02; G01S 7/027
See application file for complete search history.

(56) References Cited

U.S. PATENT DOCUMENTS

| | | | |
|---|---|---|---|
| 2006/0191825 A1* | 8/2006 | Veltri | G01F 15/18 210/85 |
| 2014/0137656 A1* | 5/2014 | Henzler | G01D 11/245 73/756 |
| 2017/0222115 A1* | 8/2017 | Kurihara | H04Q 9/00 |
| 2018/0195995 A1* | 7/2018 | Chen | G01N 33/0047 |

FOREIGN PATENT DOCUMENTS

DE           10346626 A1 *  5/2005  .......... G01D 11/245

* cited by examiner

*Primary Examiner* — Benjamin R Schmitt
(74) *Attorney, Agent, or Firm* — Jonathan Kidney; Intelink Law Group, P.C.

(57) ABSTRACT

An environmental sensor device with a sensor enclosure is configured for use in a gas environment. An enclosure support, at least one sensor on a face of the enclosure; and at least one debris sloughing structure is used. The debris sloughing structure is composed of a channel with a set of inner and outer ridges disposed in the enclosure around a periphery of the at least one sensor, wherein a top portion of the debris sloughing structure above the at least one sensor and lateral portions of the debris sloughing structure on lateral sides of the at least one sensor. A shape and arrangement of the debris sloughing structure carries condensate or contaminants forming on non-sensor areas of the enclosure away from the sensor and to a bottom portion of the enclosure.

20 Claims, 3 Drawing Sheets

SENSOR HOUSING WITH DEBRIS SLOUGHING STRUCTURE

CROSS-REFERENCE TO RELATED APPLICATION(S)

This application claims the benefit of U.S. Provisional Patent Application No. 62/967,511, filed Jan. 29, 2020, the contents of which are hereby incorporated by reference in its entirety.

FIELD

This invention relates to an environment sensing device. More particularly, it relates to a debris sloughing structure for an environment sensing device.

BACKGROUND

Gases and particle suspensions in air are often measured to determine the current conditions in an infrastructural void. The void could be in a tank, in a pipe, in a manhole, vault, or workspace, etc. The air carries the gases and suspensions throughout the void and onto a sensor. Typically, the sensor will have direct contact with the air, or be behind a protective filter or screen. Moisture can condense on supporting structures, cabling, connectors, void walls and roof. This moisture can carry contamination across the face of the sensor or protective filter. Further, the moisture could evaporate leaving solutes and suspensions. These deposits of contamination could interfere physically or chemically with the sensor and affect its accuracy and function.

Therefore, there has been a longstanding need in the sensing discipline for structures and/or systems that minimize or prevent the contamination of sensors from contact-related contamination. Various structures and/or systems for addressing this challenge is elucidated in the following description and figures.

SUMMARY

The following presents a simplified summary in order to provide a basic understanding of some aspects of the claimed subject matter. This summary is not an extensive overview, and is not intended to identify key/ritical elements or to delineate the scope of the chinned subject matter. Its purpose is to present some concepts in a simplified form as a prelude to the more detailed description that is presented later.

In one aspect of the disclosed embodiments, an environmental sensor device is provided, comprising: a sensor enclosure configured for use in a gas environment; an enclosure support; at least one sensor disposed on a predominantly vertical face of the enclosure; and at least one debris sloughing structure composed of a channel with a set of inner and outer ridges disposed in the enclosure around a periphery of the at least one sensor, a top portion of the debris sloughing structure above the at least one sensor and lateral portions of the debris sloughing structure on lateral sides of the at least one sensor, wherein a shape and arrangement of the debris sloughing structure carries condensate or contaminants forming on non-sensor areas of the enclosure away from the sensor and to a bottom portion of the enclosure.

In another aspect of the disclosed embodiments, the above device is provided, wherein the at least one sensor is an Oxygen, Methane, Volatile Organic Compounds (VOC), Hydrocarbon, Hydrogen Sulfide (IIS), Carbon Monoxide (CO), Sulphur Dioxide ($SO_2$), acoustic, motion, depth, radar, laser, or optical sensor; and/or wherein at least one of the debris sloughing structure and a face of the enclosure is hydrophobic; and/or the enclosure support is a cable attached to a top of the enclosure, the cable conveying at least one of data and power; and/or wherein the enclosure is attached to a vertical wall or other physical structure; and/or wherein the debris sloughing structure is in the shape of a diamond; and/or wherein the debris sloughing structure is in the shape of a circle or oval; and/or where the enclosure carries its own power source and a wireless transmitter; and/or further comprising a hood disposed on a top of the enclosure; and/or wherein the enclosure is disposed within a manhole; and/or further comprising a protective cover secured over the at least one sensor; and/or wherein the cover is a screen; and/or wherein the vertical face of the enclosure is composed of a plurality of differently angled vertical faces; and/or further comprising a tube attached to a bottom of the at least one debris sloughing structure or enclosure.

In yet another aspect of the disclosed embodiments, a method of removing condensate forming on a sensor enclosure is provided, comprising: forming a debris sloughing structure around a periphery of a sensor disposed in a predominantly vertical face of an environmental sensor enclosure, comprising: forming a channel with a set of inner and outer ridges, a top portion of the channel disposed above the sensor and lateral portions of the channel disposed on lateral sides of the sensor, wherein a shape and arrangement of the debris sloughing structure carries condensate or contaminants forming on non-sensor areas of the enclosure away from the sensor and to a bottom portion of the enclosure.

In yet another aspect of the disclosed embodiments, the above method is provided, wherein the sensor senses one of Oxygen, Methane, Volatile Organic Compounds (VOC), Hydrocarbon, Hydrogen Sulfide ($H_2S$), Carbon Monoxide (CO), Sulphur Dioxide ($SO_2$), acoustic, motion, depth, radar, laser, or optical energy; and/or further comprising attaching the enclosure to a vertical wall or other physical structure; and/or further comprising disposing a power source and wireless transmitter in the enclosure; and/or further comprising placing the enclosure in a manhole; and/or further comprising adding a gas permeable cover on the sensor.

DETAILED DESCRIPTION

The exemplary system/apparatus and method can be used for the measurement of gases or suspension in the ambient air of an enclosure, vault, chamber, pipeline, sewer manholes, underground void, or above ground void. In particular these gases could be toxic, corrosive, asphyxiating, or damaging to equipment or personnel in the void. The gases are carried by air and impinge on and enter the face of the sensor. Other contamination can be carried by the air and condense with moisture on the sensor's enclosure This moisture can condense and carry particulates, condensates, and contamination over and onto the face of the sensor. As described below, the exemplary debris sloughing structure intercepts and carries the contamination away from the sensor's face for discharge. This allows the face of the sensor to remain clean and free to transport target gases to the internal sensor for measurement. Throughout this description, the term sensor('s) enclosure is understood to refer to the outer housing which encloses the sensor(s) and is evident from the context of the description and Figs. As such, the sensor housing can be positioned into an environment which, depending on the circumstances, may be an enclosed, such as a vault, chamber, pipeline, manhole, sewer, void or other closed or partially closed space (e.g., enclosure) that offers an environment where gases may congregate.

Figure 1:
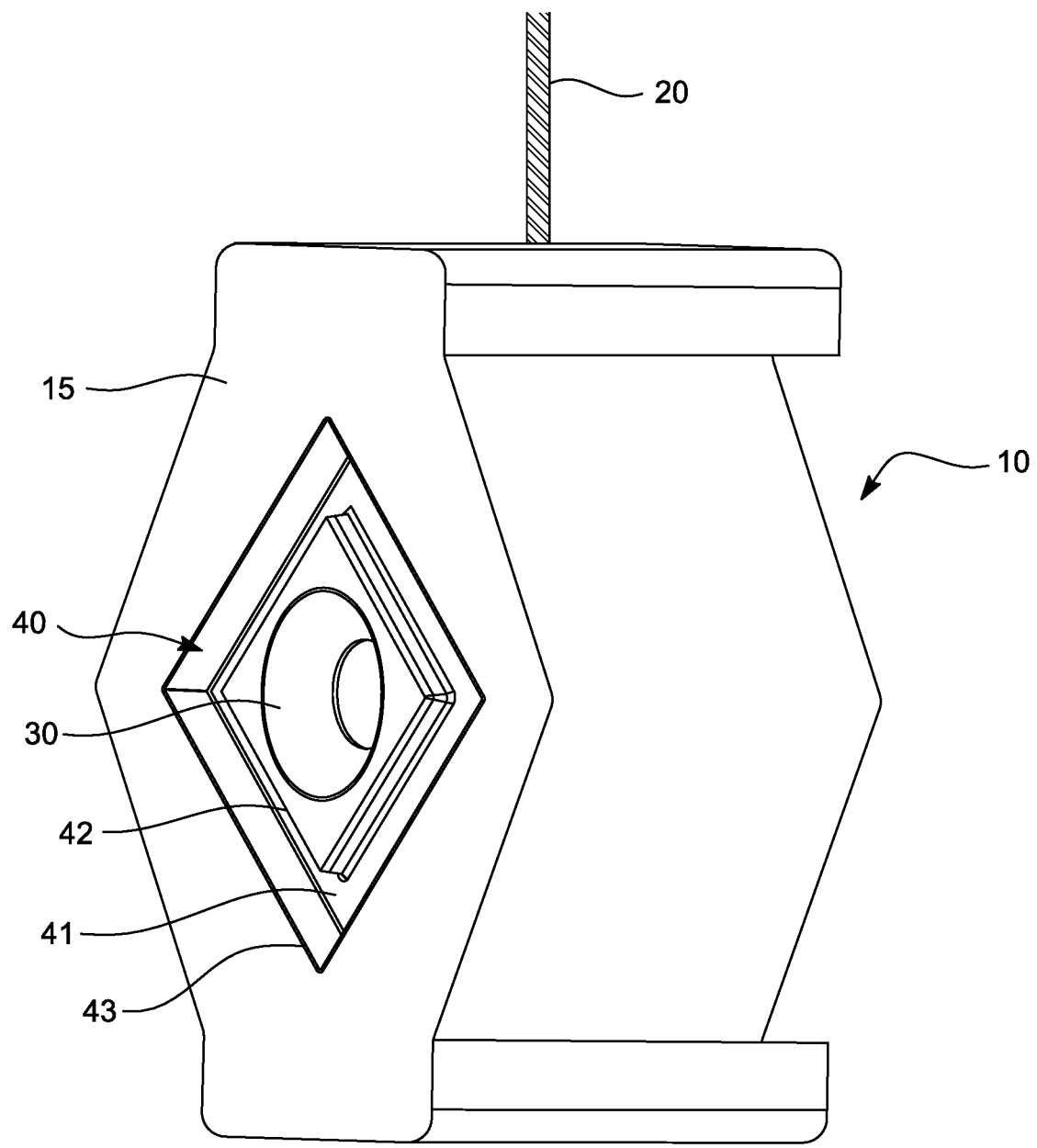
FIG. 1 is a perspective illustration showing an exemplary sensor enclosure with a debris sloughing structure.

FIG. 1 is a perspective frontal illustration showing an exemplary debris sloughing structure 40 within a sensor enclosure 10 having a sensor-side enclosure face 15, sensor(s) 30 disposed on or within the enclosure 10, and optional supporting and/or data cable 20 (referred hereafter generically as cable 20) coupled to the enclosure. There may be more than one sensor(s) 30 and its location(s) on the enclosure 10 may vary according to design preference. It should be noted that sensor(s) 30 in many instances includes a protective screen (e.g., grid, etc.) or cover on a face of the sensor(s) 30. For ease of explanation, when referencing sensor(s) 30, the description may implicitly include the protective screen/cover when such a protective screen/cover is used.

Enclosure 10 is understood to for use in an environment containing gases and is shown here as a polygonal box, however it may be circular, triangular, and so forth. Cable 20 is illustrated as supporting the enclosure 10, however, other means of support may be used. Non-limiting examples of alternative support can be a shelf, multiple cables, hooks, fixtures for attachment and so forth. In a wireless version, the enclosure would have a transmitter and the support mechanism would not need to also provide data transfer ability. It is noted here that cable 20 may also supply power, if so desired. In other embodiments, multiple cables 20 may be utilized, some providing power and/or data while some providing support, etc. As is apparent, various changes to the configuration of the respective cable 20 as well as the shape of the enclosure 10, may be implemented and are within the scope of one of ordinary skill in the art. Therefore, such modifications are understood to be within the purview of this disclosure.

Cable 20 is illustrated as one of many possible support examples and shows that moisture and/or contamination may flow from the top/surrounds of the cable 20 to the top of the enclosure 10 and subsequently may flow across a face of the sensor 30. Alternately moisture could condense on another surface of the enclosure 10 and depending on the shape of the enclosure 10, accumulate to flow over the sensor(s) 30. For example, moisture may condense on sensor-side enclosure face 15 and flow over the sensor(s) 30. Further, the environment that the exemplary sensor device is occupying could have water/liquid sprayed onto the enclosure 10 or sensors) 30) or leaked in with additional moisture and/or contaminants collecting on the enclosure 10 or sensor(s) 30.

A debris sloughing structure 40 on the sensor-side enclosure face 15 eliminates or mitigates the effect of the above contamination. The debris sloughing structure 40 is capable of collecting moisture by one or more of surface tension and/or capillary action and carries the moisture by gravity to the bottom of the debris sloughing structure 40. Here it gathers until it can drip off the bottom of the enclosure 10, The debris sloughing structure 40 is able to carry the moisture and contamination around and below the face(s) of sensor(s) 30 without interfering with the sensor(s)' 30 operation. It is understood that the sensor-side enclosure face 15 can be predominately on a vertical or near vertical face of the enclosure 10, so that gravity will naturally force the collected moisture to move down the debris sloughing structure 40.

In some embodiments, a hydrophobic coating or contaminant-repelling material can be used to help "accelerate" the process. Not shown, but possible is a tube or bottom channel (full or partial) at a bottom portion of the debris sloughing structure 40 to help move the accumulation off of the enclosure 10, as well as a hood of some sorts (separate from or connecting to the debris sloughing structure 40) to shield the upper portion thereof. The optional hood may be made of a material or configured to be "transparent" to the sensor(s) 30. Similarly, a grid or "covering" may be placed over the sensor(s) 30 that also provides protection from contamination and/or moisture. One such configuration could have the hood, or grid (or combination) be structured to "channel" or direct contamination and/or moisture to some portion of the debris sloughing structure 40.

The exemplary debris sloughing structure 40 can be applied to a multitude of sensors, for example, sensors for Oxygen, Methane, Volatile Organic Compounds (VOC), and General Hydrocarbon sensors, as well as for acoustic, motion, depth sensing, radar, laser, optical sensors, and so forth. Not limiting examples of common sensor types are Hydrogen Sulfide ($H_2S$), Carbon Monoxide (CO), Sulphur Dioxide (502), etc. Of course, the above list is not an exhaustive list, but simply provided to show the breath of applicability of this invention to various sensors. Thus, any sensor whose performance can be affected by contamination and who could benefit from the debris sloughing structure 40 can be utilized.

FIG. 1's illustration shows one possible debris sloughing structure shape where it is shaped as a "diamond" with a channel 41 with interior ridge 42 and exterior ridge 43. The shape is understood to be exemplary, however, it is understood other shapes may be utilized, non-limiting examples being an oval, vase-like, circle, and so forth. The used shape should have the ability to direct the "intruding" fluid/gases to move around and down away from the sides of the sensor(s) 30, being laterally protected from the moving fluid/gases via the ridges 42, 43. Of course, the ridges 42, 43 may be only be on the top/sides portions of the debris sloughing structure 40. Further, the debris sloughing structure 40, being shown as "centered" around a face of the sensor(s) 30, may be offset in any manner desired, according to design preference. Additionally, multiple debris sloughing structures can be used with differing ridge heights, as well as shapes and orientations. For example, for a multiple sensor housing may have several debris sloughing structures where each of the "higher" debris sloughing structures are configured to channel to the "lower" or adjacent debris sloughing structure.

It should be noted, that while the debris sloughing structure 40 is shown as having sections with smooth faces, or vertical faces, it may designed to have channels or other features within the debris sloughing structure 40 as well as having the face in a semi-vertical orientation (e.g., acute, obtuse angle or negative angle—to have a top of the debris sloughing structure inclined or cliff-like compared to the bottom of the debris sloughing structure). Additionally, the face of the debris sloughing structure 40 may be faceted, if so desired.

Figure 2:
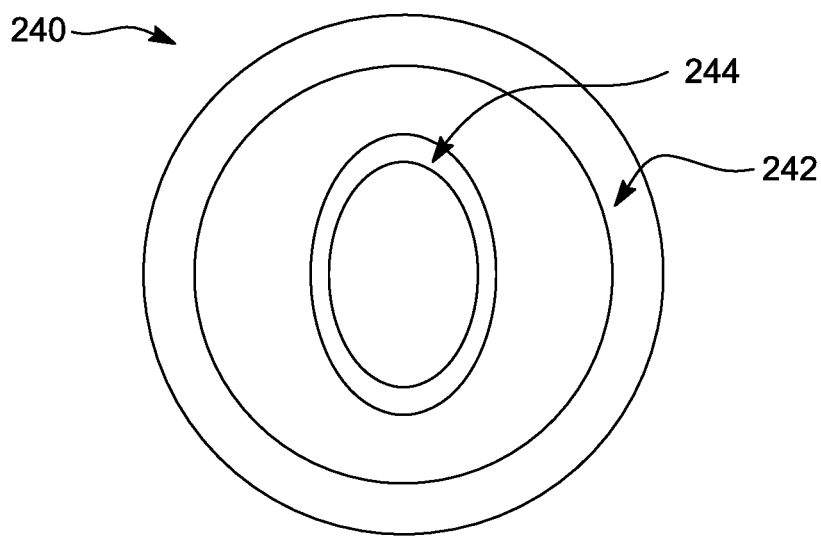
FIG. 2 is an illustration of a composite debris sloughing structure containing two different ridge shapes.

FIG. 2 is an illustration of a composite debris sloughing structure 240 containing two different channel shapes, outer circular 242 and inner oval 244. It is presumed that a sensor (not shown) is disposed in the interior of inner oval 244. This illustration provides one non-limiting example of a variation of the debris sloughing structures that are possible.

Figure 3:
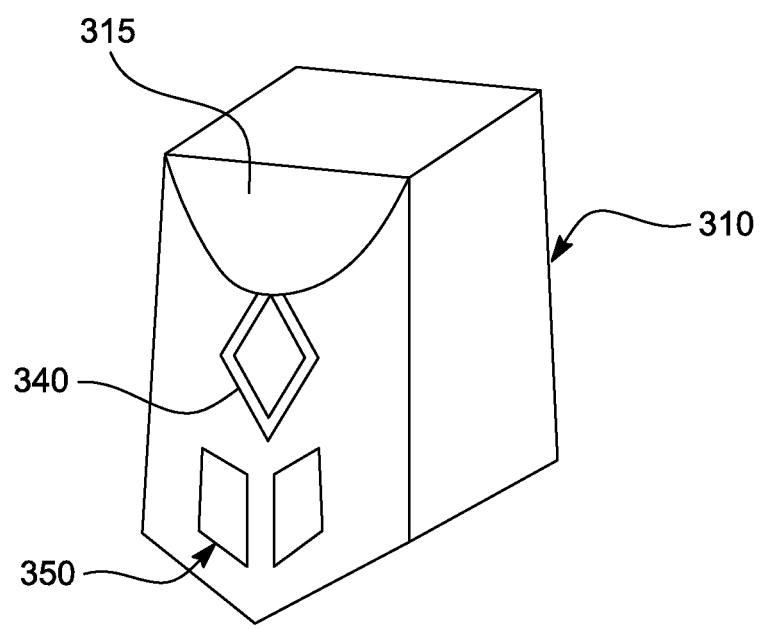
FIG. 3 is an illustration of another embodiment of an exemplary enclosure with a hood.

FIG. 3 is an illustration of another embodiment of an exemplary enclosure 310 with a hood 315. The hood 315 helps to shield the debris sloughing structure 340 (it is presumed that a sensor (not shown) is disposed in the interior of the debris sloughing structure 340). Facets or alternate surfaces 350 below the debris sloughing structure 340 operate to help channel any condensate coming off the bottom of the debris sloughing structure 340 to the bottom of the enclosure 310.

Figure 4:
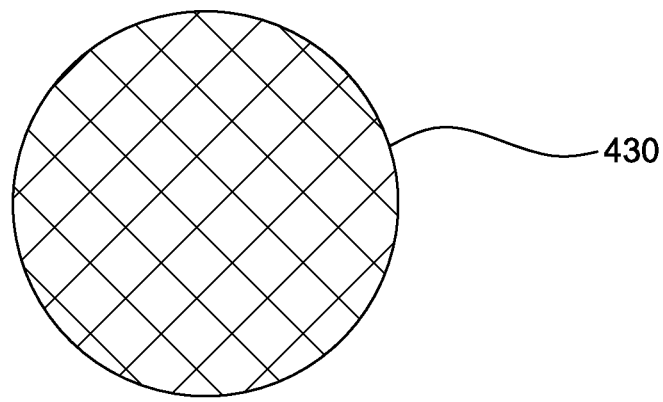
FIG. 4 is an illustration of one possible sensor shield or cover.

FIG. 4 is an illustration of one possible sensor shield or cover 430. Here, it is illustrated with a screen or grid like appearance. In other embodiments, the grid may have apertures in the shape of circular holes, and so forth.

Figure 5:
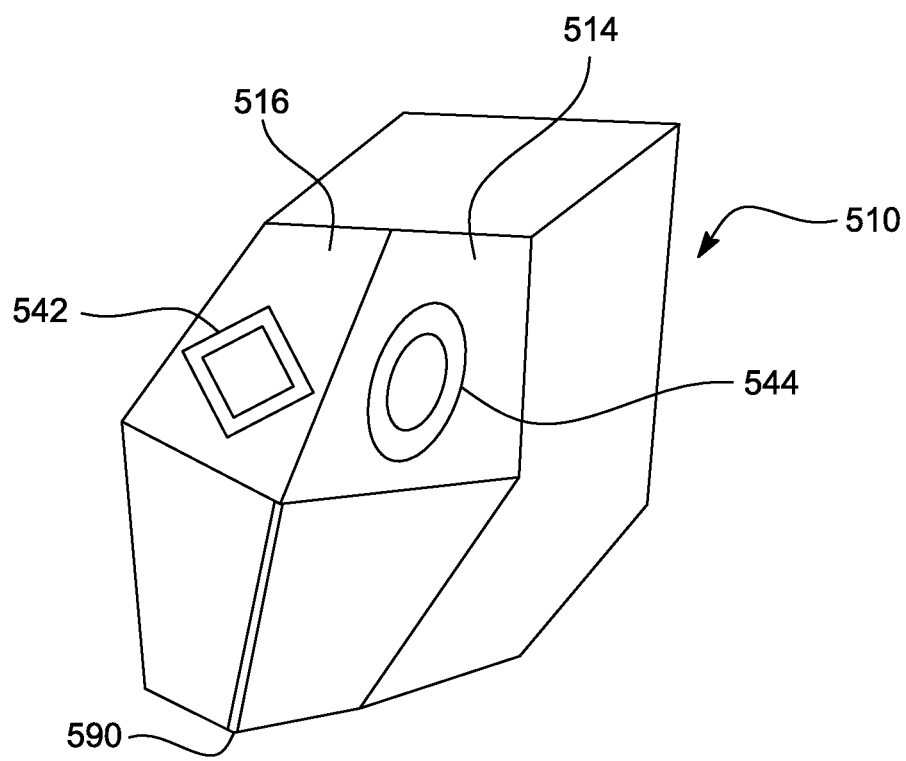
FIG. 5 is an illustration of another embodiment of an exemplary enclosure with faceted faces and differing debris sloughing structures.

FIG. 5 is an illustration of another embodiment of an exemplary enclosure 510 with faceted faces 514, 516 and differing debris sloughing structures 542, 544, respectively. A channel or tube 590 operates to funnel condensate from the faceted faces 514, 516 to the bottom of the enclosure 510.

In view of the above disclosure, it is understood that many modifications and variations can be made without departing from its scope, as will be apparent to those skilled in the art. Therefore, the present disclosure is not to be limited in terms of the particular embodiments described in this application, which are intended as illustrations of various aspects.

What is claimed is:

1. An environmental sensor device, comprising:
    a sensor housing configured for use in a gas environment, having a predominately vertical face;
    a sensor housing support;
    at least one sensor disposed on the predominately vertical face; and
    at least one debris sloughing structure having a channel with a set of inner and outer ridges disposed around a periphery of the at least one sensor, a top portion of the debris sloughing structure displaced downward and distal from an upper end of the predominately vertical face and above the at least one sensor, a bottom portion of the debris sloughing structure displaced upward and distal from a lower end of the predominantly vertical face and below the at least one sensor, and lateral portions of the debris sloughing structure on lateral sides of the at least one sensor,
    wherein a shape and arrangement of the debris sloughing structure is configured to carry condensate or contaminants forming on non-sensor predominately vertical face areas above the debris sloughing structure to the lower end of the predominantly vertical face.

2. The device of claim 1, wherein the at least one sensor is an Oxygen, Methane, Volatile Organic Compounds (VOC), Hydrocarbon, Hydrogen Sulfide ($H_2S$), Carbon Monoxide (CO), Sulphur Dioxide ($SO_2$), acoustic, motion, depth, radar, laser, and optical sensor.

3. The device of claim 1, wherein at least one of the debris sloughing structure and a face of the sensor housing is hydrophobic.

4. The device of the claim 1, wherein the sensor housing support is a cable attached to a top of the sensor housing, the cable conveying at least one of data and power.

5. The device of claim 1, wherein the sensor housing is attached to a vertical wall or other physical structure.

6. The device of claim 1, wherein the debris sloughing structure is in the shape of a diamond.

7. The device of claim 1, wherein the debris sloughing structure is in the shape of a circle or oval.

8. The device of claim 1, where the sensor housing carries its own power source and a wireless transmitter.

9. The device of claim 1, further comprising a hood disposed on a top of the sensor housing.

10. The device of claim 1, further comprising a manhole, wherein the sensor housing is disposed within the manhole.

11. The device of claim 1, further comprising a protective cover secured over the at least one sensor.

12. The device of claim 11, wherein the protective cover is a screen.

13. The device of claim 1, wherein the vertical face of the sensor housing is composed of a plurality of differently angled vertical faces.

14. The device of claim 1, further comprising a tube attached to a bottom of the at least one debris sloughing structure or sensor housing.

15. A method of removing condensate forming on a sensor, housing comprising:
    forming a debris sloughing structure around a periphery of at least one sensor disposed in a predominantly vertical face of an environmental sensor housing, comprising:
    forming a channel with a set of inner and outer ridges, a top ridge of the channel disposed above the at least one sensor and lateral portions of the channel disposed on lateral sides of the at least one sensor, wherein the top ridge is displaced downward and separated from a top of the housing,
    wherein a shape and arrangement of the debris sloughing structure is configured to carry condensate or contaminants forming on non-sensor areas on the predominately vertical face above the debris sloughing structure away from the at least one sensor to a bottom portion of the predominately vertical face.

16. The method of claim 15, wherein the at least one sensor senses one of Oxygen, Methane, Volatile Organic Compounds (VOC), Hydrocarbon, Hydrogen Sulfide ($H_2S$), Carbon Monoxide (CO), Sulphur Dioxide ($SO_2$), acoustic, motion, depth, radar, laser, or optical energy.

17. The method of claim 15, further comprising attaching the sensor housing to a vertical wall or other physical structure.

18. The method of claim 15, further comprising disposing a power source and wireless transmitter in the sensor housing.

19. The method of claim 15, further comprising disposing the sensor housing within a manhole.

20. The method of claim 15, further comprising adding a gas permeable cover on the at least one sensor.

* * * * *